United States Patent [19]

Wojtowicz et al.

[11] 4,356,303
[45] Oct. 26, 1982

[54] SINGLE STEP PROCESS FOR CYANURIC ACID

[75] Inventors: John A. Wojtowicz, Cheshire; Haywood Hooks, Jr., West Haven, both of Conn.

[73] Assignee: Olin Corporation, New Haven, Conn.

[21] Appl. No.: 279,653

[22] Filed: Jul. 2, 1981

[51] Int. Cl.³ ............................................. C07D 251/32
[52] U.S. Cl. ................................................... 544/192
[58] Field of Search ......................................... 544/192

[56] References Cited

U.S. PATENT DOCUMENTS 4,220,769  9/1980  Smialek et al. ...................... 544/192
4,223,140  9/1980  Hirdler et al. ....................... 544/192

*Primary Examiner*—John M. Ford
*Attorney, Agent, or Firm*—James B. Haglind; Donald F. Clements

[57] ABSTRACT

Cyanuric acid is produced in a process in which a solution of urea or biuret is pyrolyzed by contacting the solution with a heated gas at temperatures which substantially pyrolyze urea or biuret while concurrently evaporating the solvent.

The novel process simplifies solvent recovery, reduces solvent losses and has reduced requirements for processing equipment.

18 Claims, No Drawings

SINGLE STEP PROCESS FOR CYANURIC ACID

This invention relates to the production of cyanuric acid. More particularly, this invention relates to the production of cyanuric acid by the pyrolysis of urea in a solvent.

Cyanuric acid, a commercially available product, can be produced by the pyrolysis of urea or biuret. The pyrolysis reaction can be carried out in the presence or absence of a liquid solvent. Prior art processes in which a liquid solvent is employed have required at least three steps. In the first step, molten urea is added to the solvent to form a reaction mixture which is maintained at temperatures suitable for pyrolyzing the urea to cyanuric acid. The cyanuric acid produced is then recovered in the second step by separation methods such as filtration or centrifugation. Drying of the cyanuric acid, the third step, is then required. In addition, purification methods are required to remove residual solvent from the cyanuric acid.

The processes of the prior art require separate apparatus for the pyrolysis reaction and the separation of the product from the solvent. To minimize solvent decomposition, the pyrolysis is conducted under reduced pressures whch make process control more difficult and increases process operating costs. Solvent losses are increased by requiring separate handling at each of the various steps of the process. Further the choice of solvents is limited to those in which cyanuric acid has a limited solubility.

There is need, therefore, for a process in which solvent recovery is simplified, solvent losses are reduced and having reduced requirements for processing equipment.

It is an object of the present invention to provide a solvent process for producing cyanuric acid from urea in which the pyrolysis reaction and solvent recovery occur substantially simultaneously.

Another object of the present invention is to provide a solvent process for producing cyanuric acid having simplified solvent recovery.

A further object of the present invention is to provide a solvent process for cyanuric acid having reduced requirements for processing equipment.

These and other objects of the invention are accomplished in a process for producing cyanuric acid by the pyrolysis of a solution of a nitrogen-containing compound selected from the group consisting of urea, biuret, and mixtures thereof, in a solvent therefore, characterized by the improvement which comprises feeding droplets of the solution into a gas heated to a temperature sufficient to pyrolyze the nitrogen-containing compound to solid particles of cyanuric acid while substantially simultaneously vaporizing the solvent into said gas to form a gaseous mixture, and recovering the cyanuric acid particles.

More in detail, the novel process of the present invention employs urea or biuret or mixtures thereof. In order to simplify the disclosure, the novel process will be described hereafter in terms of urea, a preferred embodiment of the reactant.

Any suitable form of urea may be used including solid forms such as granules, prills, or liquid molten urea. Prior to pyrolysis, the urea is dissolved in a solvent to form a solution of urea.

Any solvent may be used in which urea is suitably soluble and which has a boiling point within the pyrolysis temperature range. Generally suitable solvents include organic solvents such as alkyl pyrrolidones, cycloalkyl pyrrolidones, alkyl oxazolidones, dialkyl sulphones, cycloalkyl sulphones, including those substituted by alkyl and cycloalkyl groups containing up to about 6 carbon atoms; lower acyl amides; phenols and cresols; glycols and glycol ethers; and alicyclic alcohols. Specific examples of suitable solvents include N-cyclohexyl pyrrolidone, N-methyl pyrrolidone, N-ethyl pyrrolidone, N-isopropyl pyrrolidone, N-butyl pyrrolidone, 1-isopropyl-4-methyl-2-pyrrolidone, 5-methyl-2-oxazolidone, 3,4-dimethyl-2-oxazolidone, dimethyl sulphone, dipropyl sulphone, sulpholane, methyl sulpholane, dimethyl sulpholane, o-cresol, p-cresol, dimethyl formamide, dibutyl formamide and dimethylacetamide, diethylene glycol, dipropylene glycol, diethylene glycol monomethyl ether, triethylene glycol ethyl ether, tetrahydrofurfuryl alcohol, methyl cyclohexanol, and trimethyl cyclohexanol. Mixtures of the suitable solvents may be employed, however, this may require means for solvent separation.

Urea is dissolved in the solvent to form solutions of urea which can be fed to a reactor to be pyrolyzed by contact with hot gases. Solutions having urea concentrations, for example, in the range of from about 2 to about 60, preferably from about 3 to about 30, and more preferably from about 5 to about 15 percent by weight of urea may be employed.

Prior to being fed to the pyrolysis reactor, the urea solution is maintained at temperatures below those at which pyrolysis and solvent evaporation take place, i.e., below about 150° C. The solution is fed into the reactor by any suitable means such as gravity flow, spraying, injection, etc.

The heated gas fed to the reactor to contact the urea solution is any gas which is non-reactive with urea, the solvent or cyanuric acid. Suitable examples of the heated gas include ammonia, nitrogen, or carbon dioxide. Air may also be used if the solvent is essentially resistant to oxidation. The heated gas is maintained at temperatures sufficient to pyrolyze urea and to vaporize the solvent; these being dependent on the solvent employed, the concentration of the urea solution and the like.

The single step pyrolysis and solvent separation process of the present invention may be carried out in any suitable reactor in which droplets of the urea solution can be contacted with a hot gas. Suitable reactors include, for example, moving bed reactors such as fluidized bed reactors or stirred bed reactors, spray dryers or spray grainers, rotary kilns, pan granulators, etc.

In one embodiment, the urea solution is fed in finely divided droplet form onto a moving bed of particles of granular cyanuric acid. The bed may be agitated by mechanical means such as motor driven agitators, lifters in a rotary drum, or the like.

In a fluidized bed reactor, the bed particles are suspended within the apparatus by means of heated gas which is fed to the reactor under sufficient pressure and velocity to maintain a moving bed of, for example, cyanuric acid particles. The urea solution is fed to the moving bed, for example, by spraying, onto the cyanuric acid particles. The heated gas simultaneously pyrolyzes the urea to cyanuric acid and evaporates the solvent from the bed particles. Ammonia gas, which is formed during the pyrolysis reaction, and solvent vapors form a gaseous mixture with the heated gas. This gaseous mixture is removed from the reactor and fed to a solvent recovery vessel such as a condenser, where the solvent is recovered. Ammonia may be recovered from the gaseous mixture removed from the condenser by known methods such as liquefaction.

In a preferred embodiment, ammonia is used as the heated gas as it simplifies the recovery process. Following its removal from the solvent recovery apparatus, a portion of the $NH_3$ is recycled to the moving bed reactor; the remaining portion can be used, for example, in the production of urea.

In an alternate embodiment, the urea solution may be admixed, for example, in a screw feeder with granular particles of cyanuric acid and the resulting mixture fed to the reactor, where it is contacted with the heated gas. If desired, a portion of the cyanuric acid product may be recycled to the screw feeder.

The temperature at which the urea is pyrolyzed and the solvent vaporized is in the range of from about 150° to about 350° C., preferably from about 175° to about 300° C., and more preferably from about 200° to about 275° C. Where the process of the present invention employs a moving bed, this temperature is essentially the bed temperature.

The process is normally carried out at atmospheric pressure, however, subatmospheric or superatmospheric pressures may be employed, if desired.

Cyanuric acid particles formed are retained in the reactor for a brief period to permit any solvent attached to be substantially evaporated.

The particulate cyanuric acid product made by the novel process of the present invention is recovered from the reactor and cooled by any suitable means, such as an agitated cooling vessel employing mechanical or gas agitation means. In the cooling vessel, the agitated cyanuric acid particles are contacted with an inert gas to prevent discoloration of the cyanuric acid product. During cooling, the temperature of the cyanuric acid particle is reduced to below about 50° C., preferably in the range of from about 30° to about 40° C.

To reduce energy requirements and to reduce the formation of by-products such as ammelide and ammeline, hot solvent vapors recovered from the reactor may be fed to a concentrated urea solution to heat and dilute the solution just prior to feeding the solution to the reactor.

The cyanuric acid product of this invention can be used, for example, in the production of chloroisocyanurates, because of low concentration of ammeline and ammelide therein, which minimize concentrations of potentially dangerous nitrogen trichloride formed during the latter process.

The novel process of the present invention produces cyanuric acid in a single step in which the urea solution is pyrolyzed and substantially simultaneously the solvent is removed. Solvent recovery is simplified and solvent losses are reduced through the elimination of a separate solvent recovery operation. Equipment costs are reduced as the same reaction vessel is employed for the pyrolysis reaction and solvent evaporation. Cyanuric acid particles are produced in good yields and high assay.

A further understanding of the present invention will be provided by the following examples without any intention of being limited thereby.

EXAMPLE 1

Cyanuric acid (CA) (75 g) was charged into a one liter flask fitted with a mechanical stirrer to provide a stirred bed of CA. The flask was immersed in an oil bath maintained at 275°-290° C. While charging ammonia gas to the flask (500 cc/min.), a hot (130° C.) 12% solution of urea in N-methyl pyrrolidone was added to the flask. The urea solution, 1663 grams, was added to the stirred CA bed over a four hour period. Upon contact of the heated $NH_3$ gas with the urea solution on the CA particles, the urea was pyrolyzed to cyanuric acid and simultaneously the solvent was evaporated. The volatilized solvent was removed continuously in a mixture with the $NH_3$ gas and condensed. After addition of the urea solution was completed, heating of the stirred CA product was continued for about 15 minutes to remove traces of solvent. The cooled product weighed 215 g. The in-hand product yield (corrected for the original bed material) of CA was 84%. The remainder of the urea charged was codistilled with the volatilized solvent and recovered with the solvent upon condensation. The product was analyzed as follows:

98.2% Cyanuric Acid
1.4% Ammelide
0.3% Ammeline

EXAMPLE 2

Granular urea (454 grams) was dissolved in N-methyl pyrrolidone to form a solution containing 47 percent by weight of urea. The solution was maintained at a temperature in the range of 120° to 130° C. and was added dropwise over a 4 hour period to a fluidized bed reactor having a bed formed of granular cyanuric acid (75 grams). Nitrogen gas preheated to 235°-240° C. was passed through the bed as the fluidizing gas and maintained the bed temperature in the range of 205°-220° C. Upon contact of the urea solution with the hot nitrogen gas, the urea was pyrolyzed to cyanuric acid and simultaneously the solvent was evaporated. Following the completion of the addition of the urea solution to the reactor, a post-reaction period of about 5 minutes was employed to remove traces of solvent from the bed. The carrier gas containing solvent vapors, some urea, and by-product ammonia was passed from the reactor to a condenser where the solvent was recovered by condensation.

What is claimed is:

1. In a process for producing cyanuric acid by the pyrolysis of a solution of a nitrogen-containing compound selected from the group consisting of urea, biuret and mixtures thereof in a solvent therefore, characterized by the improvement which comprises feeding droplets of said solution into a gas heated to a temperature sufficient to pyrolyze said nitrogen-containing compound to solid particles of cyanuric acid while substantially simultaneously vaporizing said solvent into said gas to form a gaseous mixture, and recovering said cyanuric acid particles.

2. The process of claim 1 in which said temperature is in the range of from about 150° to about 350° C.

3. The process of claim 2 in which said nitrogen-containing compound is urea.

4. The process of claim 3 in which said solvent is selected from the group consisting of alkyl pyrrolidones, cycloalkyl pyrrolidones, alkyl oxazolidones, dialkyl sulphones, cycloalkyl sulphones, and sulpholane were said alkyl and cycloalkyl groups contain up to about 6 carbon atoms.

5. The process of claim 4 in which said droplets of said solution are deposited on particles comprising a moving bed.

6. A process for producing cyanuric acid which comprises:
(a) feeding droplets of a solution of urea in a solvent onto a moving bed,
(b) contacting said solution with a gas heated to a temperature sufficient to pyrolyze said urea to produce cyanuric acid particles and ammonia gas and substantially simultaneously to vaporize said solvent to form a gaseous mixture comprised of said heated gas, solvent vapors, and ammonia,
(c) removing said gaseous mixture, and
(d) recovering said cyanuric acid particles.

7. The process of claim 5 or claim 6 in which said bed is comprised of cyanuric acid particles.

8. The process of claim 7 in which said heated gas is selected from the group consisting of ammonia, nitrogen, and carbon dioxide.

9. The process of claim 8 in which said temperature is in the range of from about 175° to about 300° C.

10. The process of claim 9 in which said moving bed is a fluidized bed.

11. The process of claim 10 in which the fluidizing gas is selected from the group consisting of ammonia, nitrogen, and carbon dioxide.

12. The process of claim 9 in which said gaseous mixture is cooled to condense said solvent to liquid form and said liquid solvent is separated from the remaining uncondensed gases.

13. The process of claim 12 in which said uncondensed gases are recycled to said moving bed.

14. The process of claim 11 in which said gaseous mixture is contacted with said solution of urea prior to step (a).

15. The process of claim 7 in which said solvent is selected from the group consisting of alkyl pyrrolidones and cycloalkyl pyrrolidones where said alkyl and cycloalkyl groups contain up to about 6 carbon atoms.

16. The process of claim 7 in which said heated gas is ammonia.

17. The process of claim 16 in which said temperature is in the range of from about 200° to about 275° C.

18. The process of claim 17 in which said solvent is N-methylpyrrolidone.

* * * * *